United States Patent [19]

Finlan

[11] Patent Number: 5,055,265
[45] Date of Patent: Oct. 8, 1991

[54] BIOLOGICAL SENSORS

[75] Inventor: Martin F. Finlan, Aylesbury, England

[73] Assignee: Amersham International Plc, Buckinghamshire, England

[21] Appl. No.: 358,612

[22] Filed: May 30, 1989

[30] Foreign Application Priority Data

Jun. 6, 1988 [GB] United Kingdom ............... 8813307

[51] Int. Cl.$^5$ ..................... G01N 21/00; G01N 21/55
[52] U.S. Cl. .................. 422/82.05; 422/68.1; 422/82.09; 422/66; 356/318; 356/445; 436/44; 436/805; 435/808
[58] Field of Search ............... 422/82.05, 58, 66, 98, 422/82.09; 356/318, 445; 436/44, 805; 435/808

[56] References Cited

U.S. PATENT DOCUMENTS

| Re. 30,627 | 5/1981 | Bagshawe et al. | 422/66 |
|---|---|---|---|
| 3,526,480 | 9/1970 | Findl et al. | 422/66 |
| 4,844,613 | 7/1989 | Batchelder et al. | 356/445 |
| 4,857,273 | 8/1989 | Stewart | 422/82.05 |
| 4,877,747 | 10/1989 | Stewart | 422/58 |
| 4,883,642 | 11/1989 | Bisconte | 422/66 |

FOREIGN PATENT DOCUMENTS 2173895 10/1986 United Kingdom .

OTHER PUBLICATIONS

"Surface Plasmon Resonance for Gas Detection and Biosensing", Liedberg et al., Sensors and Actuators, 4 (1983), pp. 299–304.
"Experimental Observation of the Long-Range Surface-Plasmon Polariton", Craig et al., Optics Letters, vol. 8, No. 7, Jul. 1983, pp. 380–382.
"Long-Range Surface-Plasmon Modes in Silver and Aluminum Films", Quail et al., Optics Letters, vol. 8, No. 7, Jul. 1983, pp. 377–379.

Primary Examiner—Robert J. Warden
Assistant Examiner—Theresa A. Trembley
Attorney, Agent, or Firm—Wenderoth, Lind & Ponack

[57] ABSTRACT

The present invention is drawn to a surface plasmon resonance (SPR) sensor in which the phenomenon of long-range surface plasmon resonance is used to develop a highly sensitive detector for use in biological, biochemical or general chemical testing. The sensor includes a laminar structure having of a high refractive index glass block, a membrane of dielectric material, a thin metal layer, and a sensitive layer. A sample to be tested is brought into contact with the sensitive layer. The refractive index of the dielectric layer and that of the layer (sensitive layer/sample) on the opposite side of the metallic layer should be equal, or nearly so, and the refractive index of the glass block should be higher than this so that total internal reflection takes place at the interface between the block and the membrane. Light from a laser source is totally internally reflected at this interface, and the strength of the reflected beam is monitored by a light detector. Provided conditions are correct, long-range SPR will take place which will sensitively alter the strength of the light in dependence upon the progress of the reaction between the sensitive layer and sample.

23 Claims, 2 Drawing Sheets

BIOLOGICAL SENSORS

BACKGROUND OF THE INVENTION

This invention relates to sensors for use in biological, biochemical and chemical testing and in particular to immunosensors used to monitor the interaction of antibodies with their corresponding antigens.

When antibodies are immobilized on a surface, the properties of the surface change when a solution containing a corresponding antigen is brought into contact with the surface to thus allow the antigen to bind with the antibody. In particular, the change in the optical properties of the surface can be monitored with suitable apparatus.

The phenomenon of surface plasmon resonance (SPR) can be used to detect minute changes in the refractive index of the surface as the reaction between the antigen and the antibody proceeds. Surface plasmon resonance is the oscillation of the plasma of free electrons which exists at a metal boundary. These oscillations are affected by the refractive index of the material adjacent the metal surface and it is this that forms the basis of the sensor mechanism. Surface plasmon resonance may be achieved by using the evanescent wave which is generated when a P-polarized light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the equipment described in this paper. A beam 1 of light is applied from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs the refractive index of the layer 6 will change owing to the increased size of the antibody molecules and this change can be detected and measured using the surface plasmon resonance technique, as will now be explained.

Surface plasmon resonance can be experimentally observed, in the arrangement of FIG. 1, by varying the angle of the incident beam 1 and monitoring the intensity of the internally reflected beam 4. At a certain angle of incidence the parallel component of the light momentum will match with the dispersion for surface plasmons at the opposite surface 8 of the metal film. Provided that the thickness of metal film 5 is chosen correctly there will be an electromagnetic coupling between the glass/metal interface at surface 2 and the metal/antibody interface at surface 8 which results in surface plasmon resonance and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody layer 6—and the angle of incidence corresponding to resonance is thus a direct measure of the state of the reaction between the antibody and the antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

SUMMARY OF THE INVENTION

An object of the present invention seeks to improve on the sensitivity of the basic surface plasmon resonance sensor by utilizing the phenomenon of long range surface plasmon resonance. This phenomenon is described in a paper entitled "Long-range surface-plasmon modes in silver and aluminium films" by Quail, Rako and Simon in Optics Letters, vol. 8, page 377.

The present invention provides a sensor comprising a source of electro-magnetic radiation, a structure comprising a block of material transparent to the radiation from said source, a membrane of dielectric material positioned against a surface of said block, a layer of metallic material applied to that surface of said membrane opposite said block and a layer of sensitive material applied to said metallic layer, means for introducing onto the sensitive layer so as to react therewith a sample to be analyzed, wherein the index of refraction of said sample and/or said sensitive layer is arranged to be equal or nearly equal to that of said membrane, and wherein the index of refraction of the material of said block is higher than that of said membrane and said sample, and means for monitoring radiation from said source which is applied to said transparent block, and which is internally reflected within the structure, the arrangement being such that the radiation causes long range surface plasmon resonance to occur, the characteristics of which resonance, as detected by said monitoring means, are dependent upon the reaction between the sample and the sensitive layer.

When long range surface plasmon resonance is used, the width of the resonance dip is much smaller than that for "normal" or short range surface plasmon resonance—up to ten times smaller. The sensitivity can thus, in principle, be greater.

The transparent block may be made from high refractive index glass or polymer with a refractive index typically of 2. Typically, the refractive index of the first layer and the sample is 1.4. The fact that the block has a higher refractive index than the membrane means that a beam from the source, and incident through the block into said surface will undergo total internal reflection at the interface between the block and the membrane. At resonance, energy is coupled into the metal layer via the membrane and sets up a surface plasmon wave in the metal layer and a corresponding evanescent wave travelling largely in the membrane.

The block may take the shape of a prism or may be a plane rectangular block, or may be semicylindrical or hemispherical as described in our European patent application 0305109. Waveguide optics such as fiber optics could be used, as described in our copending European patent application 89300544.7 filed Jan. 20, 1989 and entitled "Biological Sensors". The invention is also applicable to the optical arrangements described in our copending European patent applications 89304570.8 and 89304572.4 both filed May 5, 1989, and British application 8811919.3 filed May 20, 1988, all entitled "Biological Sensors".

In order to successfully utilize the long range SPR mode, the thickness of the metal layer must be reduced over that for short range SPR, typically to approximately half. For a typical layer of silver, the thickness would be 17 nm.

The thickness of the dielectric layer is critical in obtaining a single narrow resonance dip. If the layer is too thick, multiple resonances occur whereas, if it is too thin a broad dip results. The thickness of the dielectric layer is typically 1200 nm.

Short range surface plasmon resonance results in the generation of a pair of symmetric modes at the metal interfaces on either side of the metal layer. The reduced metal thickness used in the present invention allows these modes to couple together to form a single antisymmetric mode which has a greatly reduced half-width at resonance. This is known as the long range surface plasmon resonance mode, to distinguish it from short range surface plasmon resonance. In between the two modes, combinations can occur, with both the symmetric and anti-symmetric modes existing together, giving two resonant dips, one for each mode, at difference angles of incidence.

The membrane may be optically coupled to the block by means of a suitable optical coupling fluid or grease. If the refractive index of this intermediate coupling layer is equal to that of the membrane, then this must be taken into account when assessing the thickness of the membrane since, from the point of view of the operation of the device, the intermediate coupling layer forms part of the membrane. References herein to the "membrane" should be interpreted accordingly.

The sensitive layer which is on the opposite side of the metal layer from the incoming radiation is usually very thin, typically 2 nm thick. The thickness of the sensitive layer is augmented during a test by the thickness of the liquid sample, for example serum. The thickness of the liquid sample will generally be much greater than that of the sensitive layer; indeed, in some circumstances the sensitive layer may not exist as a separate entity at all—see below. Typically the thickness of the liquid sample will be about one wavelength of the radiation—in the region of 750 nm. In these circumstances, when assessing the necessary equality of refractive index in the layers on either side of the metallic layer, it is likely that, in the case of the sensitive layer and/or sample, it is the sample which will predominate due to its vastly greater thickness. It is quite possible, however, that the sensitive layer may have sufficient thickness to predominate. In practice, the values of refractive index of the sample and the sensitive layer are likely to be pretty close.

In practice the frequency of the electromagnetic radiation will be within or near the visible region. Lasers are a suitable source of radiation.

Although the layer applied to the metal film is described herein as an antibody layer for use in immunoassays, it will be seen that any sensitive layer whose refractive index changes upon an event occurring can be used thus to provide a sensitive detector having a wide variety of applications in the fields of biology, biochemistry and chemistry. The material comprising the sensitive layer may be specific to a particular entity within the sample or may be non-specific (i.e. may interact with several species of entity within the sample). Examples of specific materials include recognition molecules such as the aforementioned antibodies which will specifically bind an analyte of interest within the sample, DNA/RNA probes which will bind with their complements in the sample liquid, or lectins, glycoproteins or enzyme substrates, all of which are capable of recognizing and binding with the other partner in a bimolecular recognition pair.

Examples of non-specific materials include hydrophobic materials, for example in the form of a monolayer of phospholipid-type molecules to capture amphipathic molecules, or hydrophilic materials which would capture polysaccharides. Indeed, it has been found that the surface of the metal film itself can form an effective non-specific binding material. Silver or gold surfaces will bind proteins or polynucleotides such as DNA or RNA without the need for any further coating and, in this case a separate sensitive layer is effectively dispensed with altogether, and the surface of the metal film itself is used directly for the capture of entities within the sample to be tested.

The metal film material is commonly silver or gold, usually applied by evaporation. The film needs to be as uniform as possible in order to cater for minute movement in the position of incidence of the incoming beam. It is assumed that a structural metal film will give the best resonance and there are various ways in which the membrane can be pretreated to improve the performance of the metal film and in particular to control the natural tendency of such films to form discontinuous islands:

1. Immersion in molten metal nitrates and other molten salts. This has the effect of introducing ions into the surface in a manner which can be structured and which can act as foci for island formation.

2. Ion bombardment to introduce nucleating sites. The removal of the more mobile ions has been demonstrated to reduce the thickness at which the evaporated film becomes continuous.

3. Electroless plating or electroplating over lightly evaporated films (0 to 100 angstroms thick). Electroless plated films survive to a greater thickness than evaporated films and could form more stable nuclei for subsequent coating.

4. Evaporating onto electroless plated films. The electroless plated films have a stronger tendency to form an island structure and to form bigger islands with greater spacing than evaporating films. This could be of advantage in tuning to light of a prescribed wavelength.

Coating performance can also be improved by:

1. Controlling the membrane surface temperature during coating. Using a higher temperature substrate increased the islands' size and the spacing between them and conversley.

2. Evaporating in the presence of a magnetic or electrostatic field or electron emission device to control the ion content of the vapor stream. The state of charge of the substrate is known to affect the island structure.

3. Controlling the angle of incidence of the evaporated vapor stream relative to the membrane surface. The mobility of the evaporated atoms and hence their ability to form bigger islands is greater when the momentum of the atoms relative to the membrane surface is increased.

BRIEF DESCRIPTION OF THE DRAWINGS

In order that the invention may be better understood, an embodiment thereof will now be described by way of example only and with reference to the accompanying drawings, in which.

DETAILED DESCRIPTION OF THE PREFERRED EMBODIMENT

Figure 1:
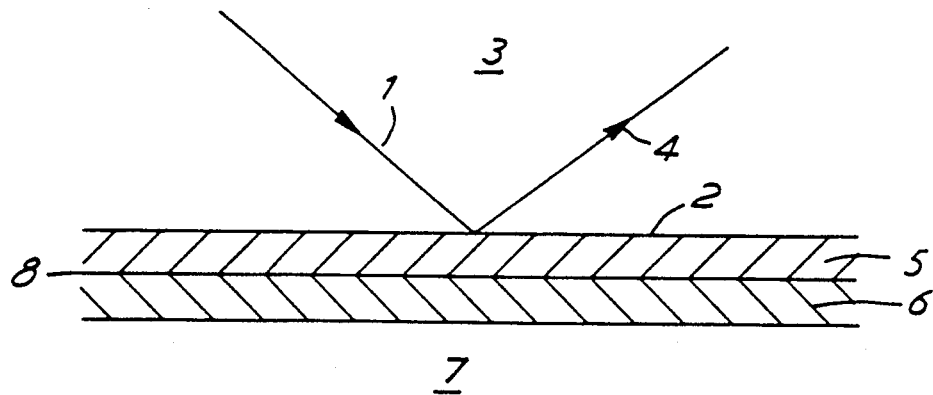
FIG. 1 is a diagram of a known experimental arrangement for demonstrating the surface plasmon resonance effect.
Figure 2:
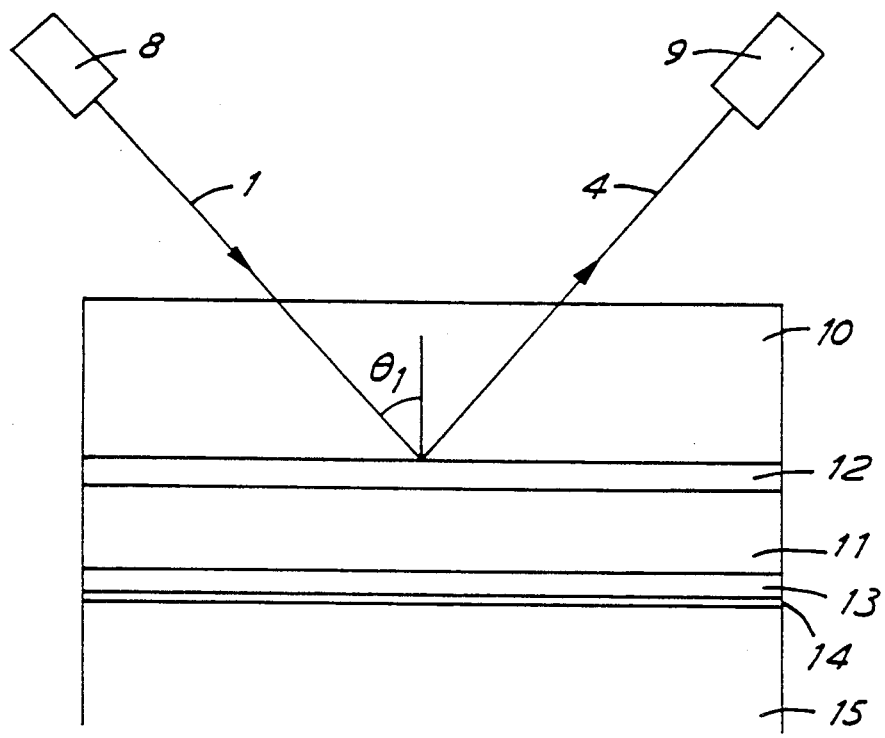
FIG. 2 is a non-scale diagram of the optical layer structure necessary to obtain long range surface plasmon resonance.

Referring to FIG. 2, there is shown a diagrammatic sectional view through the sandwich structure needed for long range surface plasmon resonance. Starting from the top in the drawing, the layers comprise a high refractive index glass or polymer block 10 of material transparent to the radiation, a membrane 11 of dielectric material such as p.t.f.e., methyl cellulose or silicone rubber optically coupled to the block 10 by an intermediate coupling layer 12 of coupling fluid or gel, a thin metal layer 13, for example of silver, a sensitive layer 14, for example an antibody layer, and a liquid layer 15 taking the form of a sample, for example serum, to be tested. The latter layer is only present during a test and reacts with the sensitive layer to alter the refractive index of the layer to thus effect the surface plasmon resonance. A radiation source 8 and radiation detector 9 complete the assembly, radiation (probably light) from the source being applied through the transparent block 10 to be internally reflected at the lower surface of the block, the reflected radiation passing out through the block and to the detector 9. As the angle $\theta_1$ of incidence of the incident beam of radiation is varied, there will be an angle at which the phenomenon of surface plasmon resonance will be observed, this manifesting itself as a sharp attenuation in the strength of the internally reflected beam. Normal (short range) surface plasmon resonance occurs at an angle $\theta_1$ of incidence to the normal of the reflecting metal layer of about 63°. For long range surface plasmon resonance, the corresponding angle is about 50°.

As mentioned above, the use of long range surface plasmon resonance has the potential for much improved sensitivity because the half width of the reflectance dip at resonance can be as much as an order less in magnitude. However, in order to achieve such improvements, the components of the arrangement shown in FIG. 2 must have certain properties:

1. The metal layer 13 should be made thinner in order to provide long range surface plasmon resonance—typically 17 nm thick, as against 56 nm thick for short range surface plasmon resonance. If the metal layer is thick symmetric modes are set upon at both metal interfaces, and extend into the metal as circulatory electron motions. If the metal layer is much thinner, however, these two modes become coupled together to form an antisymmetric mode, known as long range surface plasmon resonance, providing a very high—Q resonance effect.

2. The layers on either side of the metal layer must be index-matched. In other words, the refractive index of the material of the membrane 11 must be equal or near equal to that of the sample layer 15. Typically, the refractive index of these two layers is about 1.4.

3. The transparent block 10 must be of a material whose refractive index is high compared to that of membrane 11 and layer 15. A typical value is 2.

4. The thickness of the membrane 11 is critical in achieving a single fine resonance, as explained above. This is obtained from Fresnel's equation—see below.

In assessing the exact properties needed, it is convenient to start with the sensitive layer since it is likely that this will have a refractive index which is fixed, depending upon the particular material used. Since the sensitive layer effectively forms part of the sample from the point of view of the surface plasmon resonance, then the sample will conveniently have this same refractive index. This then sets the refractive index of the membrane to be the same as or as near as possible the same as that of the sample. The refractive index of the transparent block 10 needs to be higher than this so that total internal reflection takes place at the interface between the block 10 and the coupling layer 12/membrane 11. A suitable value for block 10 is chosen from available materials. The thickness of the membrane 11 and the metal layer 13 can now be calculated from Fresnel's equation:

$$R_{1234} = \frac{r_{12} + R_{234} \exp(i2k_{2z}d_2)}{1 + r_{12}R_{234} \exp(i2k_{2z}d_2)}$$

where $$R_{234} = \frac{r_{23} + r_{34} \exp(i2k_{3z}d_3)}{1 + R_{23}r_{34} \exp(i2k_{3z}d_3)}$$

$r_{ij}$ = Fresnel reflection coefficient for p-polarized light, as given by:

$$r_{ij} = \frac{\sqrt{\epsilon_j} \cos \theta_i - \sqrt{\epsilon_i} \cos \theta_j}{\sqrt{\epsilon_j} \cos \theta_i + \sqrt{\epsilon_i} \cos \theta_j}$$

and $$k_{iz} = \frac{\omega}{c} (\epsilon_i - \epsilon_i \sin^2 \theta_1)^{\frac{1}{2}}$$

i = dielectric constant of medium i
d = thickness of medium i
$\theta_i$, $\theta_j$ = angle of wave vector in medium i
$\omega$ = angular frequency of incident wave
c = speed of light The subscripts i, j = 1 to 4 refer to the block 10, the membrane 11, the metal layer 13 and the sample 15, respectively. Note, however, that the intermediate coupling layer 12, if present and if of the same refractive index as the membrane will effectively form part of the membrane for the purpose of this calculation. Likewise the sensitive layer will effectively form part of the sample.

As an example a typical antibody layer has an unreacted refractive index of approximately 1.4. This sets the refractive index of the sample and the membrane also at 1.4. The refractive index of the transparent block 10 is set at a convenient value higher than this, say 2. From Fresnel's equation, the following parameters can then be calculated:

Thickness of membrane 11 = 1200 nm
Thickness of metal layer 13 = 17 nm

If an intermediate coupling layer 12 of refractive index 1.4 is used, then a typical thickness for this is 200 nm, leaving a net thickness for the membrane 11 of 1000 nm.

It may be desirable to apply to the sensitive layer 14 a protective layer (not shown) of gel or similar material, such as acrylamide gel or hydrogel. During a test, such a gel will permit the antigen within a sample of, say plasma, to travel through to react with a sensitive antibody layer, but will prevent the presence of molecules in the plasma from affecting the result.

There will now be described with reference to FIG. 3, a biosensor suitable for use with the present invention. The apparatus comprises a housing 30 having a hollow interior 31 in which is positioned a printed circuit board 16 on which is mounted the electronic circuitry associated with the apparatus. An aperture is formed in the top part of the housing which aperture is covered by a support plate 17 of transparent material.

A radiation source 18 produces a collimated input beam 19 of electromagnetic radiation. The frequency of the radiation must be such as to result in the generation of surface plasmon waves and in practice will be within or near the visible region. Suitable sources include a helium neon laser or an infrared diode laser, but an ordinary light source, with suitable filters and collimators, could be used.

The light beam 19 is directed at a mirror 20 which in turn directs the light onto a concave reflecting surface 21 and thence to the transparent support plate 17. The mirror 20 is driven by motor means (not shown), to rotate in an oscillatory manner between the limit positions shown by the solid and dotted lines. The result of this is that the light beam applied to the reflecting surface 21 scans backwards and forwards between the positions represented by the beams 22 and 23.

Figure 3:
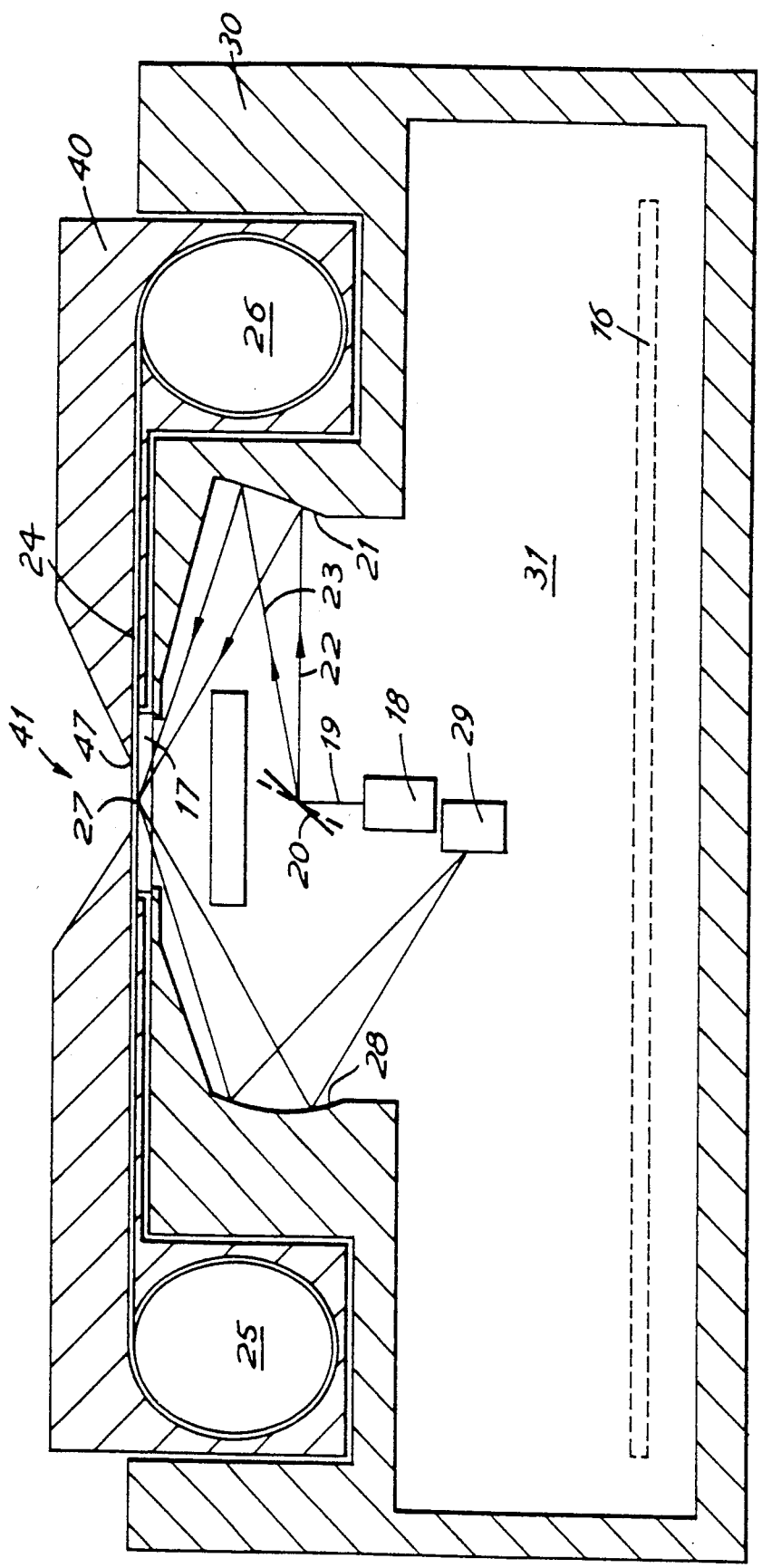
FIG. 3 is a diagram showing a typical apparatus in which the present invention may be utilized.

Positioned in the top surface of the support plate 17 is a membrane in the form of a continuous film 24 which is moveable from left to right in FIG. 3 from a supply reel 25 to a take-up reel 26. In its simplest form, the membrane takes the form of a multi-layer structure of the type shown with reference to FIG. 2; in other words comprising a flexible transparent layer, corresponding to block 10, a dielectric layer, corresponding to membrane 11, a metal film layer, for example of silver, and a final layer of sensitive material, such as an antibody layer. The arrangement is such that the layers are in the order—transparent support plate 17—flexible transparent layer—dielectric layer—metal film layer—sensitive layer. Thus the sensitive layer is on the top when seen in FIG. 3.

It will be noted that the flexible transparent layer lies directly against the transparent plate 17, possibly with an optical coupling fluid in between. Preferably the refractive index of the plate 17 is the same as that of the flexible transparent layer so that the two effectively act as a single transparent block, as far as light is concerned. In an alternative embodiment (not shown) the flexible transparent layer in the film 24 is dispensed with, reliance being placed on the support plate 17 to act as the block 10 of FIG. 2. Light incident from reflecting surface 21 behaves in the multi-layer structure in a similar manner to that described above with reference to FIG. 2. The light is internally reflected at a point 27 lying on the interface between the flexible transparent layer and the dielectric layer of the film 24. The internally reflected light passes out of the plate 17 and is reflected off a further concave reflecting surface 28 to be incident on the sensitive surface of a light detector 29.

The reflective surface 21 has a shape which is such as to bring light incident thereon from a range of angles to a single point 27, despite the refraction which inevitably occurs when the light enters the transparent plate 17. Computer analysis of the ray paths can derive a suitable shape for surface 21 to ensure that point 27 is stationary as the scanning between limit positions defined by beams 22, 23 occurs. Likewise, reflective surface 28 has a shape which is such as to bring light incident thereon from a range of angles to a single point at the sensitive area of detector 29.

The reflective surfaces 21, 28 are formed by machining the material, for example aluminium, of the housing 30. If the housing is not fabricated from a suitable material, the reflective surfaces 21, 28 can, of course, be formed as separate elements attached to the housing. Diamond machining of aluminium results in a highly reflective surface whose shape can be tailored, under computer control, to give whatever optical characteristics are required of it.

Provided that the conditions are correct and, in particular, that the angle of incidence of the incoming beam at the interface between the flexible transparent layer and the dielectric layer is correct, then long range surface plasmon resonance will result, causing a sharp dip in the intensity of the internally reflected light as the angle of incidence of the incoming wave is scanned by the mirror 20. A picture of the whole dip can thus be built up by the detector 29 by relating the detector output, on a time basis, with the scanning movement of the mirror 20. This is carried out in the associated electronic circuitry and, since it does not particularly concern the present invention, will not be described further.

The sensitive layer is one whose refractive index changes as it reacts with a sample, in the manner described above. This changes the angle of incidence at which surface plasmon resonance occurs, and thus the reaction of a sample with the sensitive layer can be monitored by observing the dip as the test proceeds. In order to carry out a test, it is simply necessary to place a sample to be tested on top of the sensitive layer in the area of the point 27 at which the light is incident, and observe the changes in the dip characteristics. Upon completion of the test, the film is advanced by a suitable amount, and a further test may then be carried out.

It is preferred to provide the film 24 housed in a disposable cassette 40 which incorporates an opening 41 via which sample may be placed on the exposed film.

I claim:

1. A sensor for use in biological, biochemical or chemical testing, said sensor comprising: a structure comprising a block of material, a membrane of dielectric material disposed over a surface of said block, a layer of metallic material disposed over that surface of said membrane opposite said block, and a layer of sensitive material disposed over said metallic layer; means for introducing onto the sensitive layer so as to react therewith a sample to be analyzed in which the index of refraction of the sample and/or said sensitive layer is equal or nearly equal to that of said membrane, and the index of refraction of the material of said block is higher than that of said membrane and the sample; means for generating electromagnetic radiation that is transmittable through said block of material and for directing the radiation through said block at a location within said structure in a manner which causes long range surface plasmon resonance to occur and which causes the radiation to be internally reflected by said structure from said location; and detecting means for monitoring radiation from said source which has been internally reflected within the structure and for detecting the characteristics of the resonance that are dependent upon the reaction between the sample and the sensitive layer.

2. A sensor as claimed in claim 1, wherein the transparent block is made from high refractive index glass or polymer.

3. A sensor as claimed in claim 2, wherein the thickness of the membrane is such as to prevent the occurrence of multiple resonances.

4. A sensor as claimed in claim 2, wherein said structure further comprises an intermediate optical coupling layer of fluid or grease extending between and optically coupling said membrane and said transparent block.

5. A sensor as claimed in claim 2, wherein the sensitive layer comprises an antibody layer.

6. A sensor as claimed in claim 2, wherein the thickness of said membrane and the thickness of said metal layer satisfy the following equations $$R_{1234} = \frac{r_{12} + R_{234} \exp(i2k_{2z}d_2)}{1 + r_{12}R_{234} \exp(i2k_{2z}d_2)}$$

and $$R_{234} = \frac{r_{23} + r_{34} \exp(i2k_{3z}d_3)}{1 + R_{23}r_{34} \exp(i2k_{3z}d_3)}$$

wherein $$r_{ij} = \frac{\sqrt{\epsilon_j} \cos \theta_i - \sqrt{\epsilon_i} \cos \theta_j}{\sqrt{\epsilon_j} \cos \theta_i + \sqrt{\epsilon_i} \cos \theta_j},$$

$$k_{iz} = \frac{\omega}{c} (\epsilon_i - \epsilon_i \sin^2 \theta_1)^{\frac{1}{2}},$$

$\epsilon_i$ = dielectric constant of medium i,
$d_i$ = thickness of medium i,
$\theta_{i,j}$ = angle of wave vector of p-polarized light in medium i, j,
$\omega$ = angular frequency of incident wave of p-polarized light, and
the subscripts 1 to 4, for the characters i, j, respectively represent the block, the membrane, the metal layer, and the layer with sample introduced thereon.

7. A sensor as claimed in claim 2, wherein the refractive index of the material of the transparent block is about 2.

8. A sensor as claimed in claim 3, wherein the thickness of the membrane is such as to prevent the occurrence of multiple resonances.

9. A sensor as claimed in claim 3, wherein said structure further comprises an intermediate optical coupling layer of fluid or grease extending between and optically coupling said membrane and said transparent block.

10. A sensor as claimed in claim 3, wherein the sensitive layer comprises an antibody layer.

11. A sensor as claimed in claim 3, wherein the thickness of said membrane and the thickness of said metal layer satisfy the following equations $$R_{1234} = \frac{r_{12} + R_{234} \exp(i2k_{2z}d_2)}{1 + r_{12}R_{234} \exp(i2k_{2z}d_2)}$$

and $$R_{234} = \frac{r_{23} + r_{34} \exp(i2k_{3z}d_3)}{1 + R_{23}r_{34} \exp(i2k_{3z}d_3)}$$

-continued
wherein $$r_{ij} = \frac{\sqrt{\epsilon_j} \cos \theta_i - \sqrt{\epsilon_i} \cos \theta_j}{\sqrt{\epsilon_j} \cos \theta_i + \sqrt{\epsilon_i} \cos \theta_j},$$

$$k_{iz} = \frac{\omega}{c} (\epsilon_i - \epsilon_i \sin^2 \theta_1)^{\frac{1}{2}}.$$

$\epsilon_i$ = dielectric constant of medium i,
$d_i$ = thickness of medium i,
$\theta_{i,j}$ = angle of wave vector of p-polarized light in medium i, j,
$\omega$ = angular frequency of incident wave of p-polarized light, and
the subscripts 1 to 4, for the characters i, j, respectively represent the block, the membrane, the metal layer, and the layer with sample introduced thereon.

12. A sensor as claimed in any one of claim 1, wherein the thickness of the membrane is such as to prevent the occurence of multiple resonances.

13. A sensor as claimed in claim 4, wherein said structure further comprises an intermediate optical coupling layer of fluid or grease extending between and optically coupling said membrane and said transparent block.

14. A sensor as claimed in claim 4, wherein the sensitive layer comprises an antibody layer.

15. A sensor as claimed in claim 4, wherein the thickness of said membrane and the thickness of said metal layer satisfy the following equations $$R_{1234} = \frac{r_{12} + R_{234} \exp(i2k_{2z}d_2)}{1 + r_{12}R_{234} \exp(i2k_{2z}d_2)}$$

and $$R_{234} = \frac{r_{23} + r_{34} \exp(i2k_{3z}d_3)}{1 + R_{23}r_{34} \exp(i2k_{3z}d_3)}$$

wherein $$r_{ij} = \frac{\sqrt{\epsilon_j} \cos \theta_i - \sqrt{\epsilon_i} \cos \theta_j}{\sqrt{\epsilon_j} \cos \theta_i + \sqrt{\epsilon_i} \cos \theta_j},$$

$$k_{iz} = \frac{\omega}{c} (\epsilon_i - \epsilon_i \sin^2 \theta_1)^{\frac{1}{2}}.$$

$\epsilon_i$ = dielectric constant of medium i,
$d_i$ = thickness of medium i,
$\theta_{i,j}$ = angle of wave vector of p-polarized light in medium i, j,
$\omega$ = angular frequency of incident wave of p-polarized light, and
the subscripts 1 to 4, for the characters i, j, respectively represent the block, the membrane, the metal layer, and the layer with sample introduced thereon.

16. A sensor as claimed in claim 1, wherein said structure further comprises an intermediate optical coupling layer of fluid or grease extending between and optically coupling said membrane and said transparent block.

17. A sensor as claimed in claim 6, wherein the sensitive layer comprises an antibody layer.

18. A sensor as claimed in claim 6, wherein the refractive index of the intermediate layer is equal to that of the membrane.

19. A sensor as claimed in claim 7, wherein the sensitive layer comprises an antibody layer.

20. A sensor as claimed in claim 1, wherein the sensitive layer comprises an antibody layer.

21. A sensor as claimed in claim 20, wherein the thickness of said membrane and the thickness of said metal layer satisfy the following equations $$R_{1234} = \frac{r_{12} + R_{234} \exp(i2k_{2z}d_2)}{1 + r_{12}R_{234} \exp(i2k_{2z}d_2)}$$

and $$R_{234} = \frac{r_{23} + r_{34} \exp(i2k_{3z}d_3)}{1 + R_{23}r_{34} \exp(i2k_{3z}d_3)}$$

wherein $$r_{ij} = \frac{\sqrt{\epsilon_j} \cos \theta_i - \sqrt{\epsilon_i} \cos \theta_j}{\sqrt{\epsilon_j} \cos \theta_i + \sqrt{\epsilon_i} \cos \theta_j},$$

$$k_{iz} = \frac{\omega}{c} (\epsilon_i - \epsilon_i \sin^2 \theta_1)^{\frac{1}{2}},$$

i = dielectric constant of medium i,
$d_i$ = thickness of medium i,
$\theta_{i,j}$ = angle of wave vector of p-polarized light in medium i,j,
$\omega$ = angular frequency of incident wave of p-polarized light, and
the subscripts 1 to 4, for the characters i, j, respectively represent the block, the membrane, the metal layer, and the layer with sample introduced thereon.

22. A sensor as claimed in claim 21, wherein said structure further comprises an intermediate optical coupling layer of fluid or grease extending between and optically coupling said membrane and said transparent block.

23. A sensor as claimed in claim 5, wherein the sensitive layer comprises an antibody layer.

* * * * *